(12) United States Patent
Theocharis et al.

(10) Patent No.: US 8,965,709 B2
(45) Date of Patent: Feb. 24, 2015

(54) COMPOSITIONS AND METHODS FOR TREATING GROWTH HORMONE DEFICIENCY

(75) Inventors: Theo Theocharis, Cologne (DE); Sylvain Larroque, Saint Julien en Genevois (FR); Laurence Bernard, Ferney Voltaire (FR)

(73) Assignee: Merch Serono SA, Coinsins, Vaud (CH)

( * ) Notice: Subject to any disclaimer, the term of this patent is extended or adjusted under 35 U.S.C. 154(b) by 286 days.

(21) Appl. No.: 13/392,128

(22) PCT Filed: Aug. 30, 2010

(86) PCT No.: PCT/EP2010/062652
§ 371 (c)(1),
(2), (4) Date: Feb. 24, 2012

(87) PCT Pub. No.: WO2011/026815
PCT Pub. Date: Mar. 10, 2011

(65) Prior Publication Data
US 2012/0149644 A1     Jun. 14, 2012

(30) Foreign Application Priority Data
Sep. 2, 2009   (EP) ................................... 09169251

(51) Int. Cl.
*G01N 33/48*   (2006.01)
*G01N 33/74*   (2006.01)
*A61K 38/27*   (2006.01)
*C12Q 1/68*    (2006.01)

(52) U.S. Cl.
CPC ............... *G01N 33/74* (2013.01); *A61K 38/27* (2013.01); *C12Q 1/6883* (2013.01); *C12Q 2600/118* (2013.01); *G01N 2333/4745* (2013.01); *G01N 2333/65* (2013.01); *G01N 2800/52* (2013.01); *G01N 2800/60* (2013.01)

USPC .......................................................... 702/19

(58) Field of Classification Search
USPC .......................................................... 702/19
See application file for complete search history.

(56) References Cited

PUBLICATIONS

Ranke, M. B. et al. "Predicting growth in response to growth hormone treatment" *Growth Hormone & IGF Research*, Feb. 1, 2009, pp. 1-11, vol. 19, No. 1.
Kawai, N. et al. "Serum Free Insulin-Like Growth Factor I (IGF-I), Total IGF-I, and IGF-Binding Protein-3 Concentrations in Normal Children and Children with Growth Hormone Deficiency" *Journal of Clinical Endocrinology and Metabolism*, Jan. 1, 1999, pp. 82-89, vol. 84, No. 1.
Darendeliler, F. et al. "Effects of Growth Hormone on Growth, Insulin Resistance and Related Hormones (Ghrelin, Leptin and Adiponectin) in Turner Syndrome" *Hormone Research*, 2007, pp. 1-7, vol. 68, No. 1.
Jorgensen, J. et al. "Short-Term Tools to Measure Responsiveness to Growth Hormone Replacement" *Hormone Research*, 2001, pp. 40-43, vol. 55, Supp. 2.
Davenport, M. et al. "Growth Hormone Treatment of Early Growth Failure in Toddlers with Turner Syndrome: A Randomized, Controlled, Multicenter Trial" *The Journal of Clinical Endocrinology & Metabolism*, Sep. 2007, pp. 3406-3416, vol. 92, No. 9.
Rosenfeld, R. "The Future of Research into Growth Hormone Responsiveness" *Hormone Research*, Apr. 2009, pp. 71-74, vol. 71, Supp. 2.
Geffner, M. E. et al. "Future Directions: Growth Prediction Models" *Hormone Research*, Dec. 10, 2007, pp. 51-56, vol. 68, Supp. 5.
Written Opinion in International Application No. PCT/EP2010/062652, Sep. 22, 2012, pp. 1-12.

*Primary Examiner* — Jerry Lin
(74) *Attorney, Agent, or Firm* — Saliwanchik, Lloyd & Eisenschenk

(57) ABSTRACT

The present invention relates to methods of predicting the level of response to treatment with growth hormone in an individual having Growth Hormone Deficiency (GHD) or Turner Syndrome (TS).

7 Claims, No Drawings

COMPOSITIONS AND METHODS FOR TREATING GROWTH HORMONE DEFICIENCY

CROSS-REFERENCE TO RELATED APPLICATION

This application is the U.S. national stage application of International Patent Application No. PCT/EP2010/062652, filed Aug. 30, 2010.

FIELD OF THE INVENTION

The present invention relates to biological and genetic markers associated with the early clinical response to Growth Hormone in individuals suffering from Growth Hormone Deficiency (GHD) or Turner Syndrome (TS). The present invention more particularly relates to biological and genetic markers, which can be used for a more accurate prediction of early treatment response in Growth Hormone Deficiency (GHD) or Turner Syndrome (TS).

The invention further discloses specific biological and genetic markers that are related to GHD or TS early response to growth hormone (GH) treatment as well as prediction tools and kits based on these biological and genetic markers as well as on some pre-treatment patient's characteristics. Thus, the invention can be used in predicting the response to growth hormone (GH) treatment and in designing improved treatment of GHD or TS.

BACKGROUND OF THE INVENTION

Growth Hormone Deficiency (GHD) includes a group of different pathologies all with a failure or reduction of growth hormone (GH) secretion. GHD may occur by itself or in combination with other pituitary hormone deficiencies. It may be congenital or acquired as a result of trauma, infiltrations, tumour or radiation therapy. Despite the large number of possible aetiologies, most children have idiopathic GHD. Depending on the criteria for diagnosis, the incidence of short stature associated with severe childhood GHD has been estimated to range between 1:4000 to 1:10000 live children in several studies (P C Sizonenko et al., Growth Horm IGF Res 2001; 11 (3):137-165).

Postnatal growth of children with GHD differs according to aetiology. Genetic deficiency of GHD causes progressive slowing of growth following normal growth in the first months of life. Growth failure is the major presenting sign of GHD in children, and lack of GH therapy in the case of severe GHD leads to very short stature in adulthood (GH Research Society, J. Clin. Endocrinol Metabol 2000; 85 (11): 3990-3993).

Turner (or Ullrich-Turner) syndrome (TS) is a chromosomal abnormality characterized by the absence of the entire chromosome X or a deletion within that chromosome. TS affects one in 1,500 to 2,500 live-born females. Short stature and reduced final height are observed in 95% of girls with TS. The average difference between mean adult height of normal women and that of TS adults is of 20 cm (Park E. et al, Pediatr Res 1983; 17:1-7). Reduced final height is due to a decline in height velocity after the age of 5 or 6 years (relative to unaffected girls) and to the absence of a pubertal growth spurt (Brook CGD et al., Arch Dis Child 1974; 49:789-795) due to the lack of the normal increase in GH secretion observed during puberty. The short stature in TS is not attributable to deficient secretions of GH or insulin-like growth factor I (IGF-I) (Cuttlet L et al., J Clin Endocrinol Metab 1985; 60:1087-1092), but a decreased amplitude and frequency of GH pulses have been reported after the age of 8 years in these patients (Ross J L et al., J Pediatr 1985; 106:202-206).

Recombinant DNA-derived human growth hormone (GH) is the only drug approved specifically for treatment of childhood growth failure and short stature, such as GHD, SGA (Small for Gestational Age) and TS. Current dose regimens for childhood GH therapy are based on body weight and are derived primarily from empirical experience. The response to GH treatment, short-term as well as long-term, displays considerable inter-individual variability. This is particularly evident for the endpoint of paediatric GH administration, i.e. the growth response, which varies significantly in subjects with Turner syndrome, but is also pronounced in children who are affected by GHD.

This variability can be investigated at two different levels. First, at the phenotype level, by assessing the individual growth response to GH administration by means of the biological markers of GH action commonly used in the clinical management of short stature subjects. Secondly, at the genotype level, which can be investigated by identifying the genetic factors responsible for the phenotypic variation of the response to GH intervention.

Growth prediction models attempt to predict the individual response to growth hormone treatment based on either pre-treatment characteristics or response after a short period of growth hormone administration in comparison to the group response. Pre-treatment parameters used in existing prediction models for idiopathic GHD and Turner Syndrome children receiving GH therapy include auxological criteria, indices of endogenous GH secretion, biological markers of GH action such as insulin-like growth factors (IGF) and their binding proteins (IGFBP), and bone turnover markers.

Ranke at al. (J Clin Endocrinol Metab 1999; 84 (4):1174-1183) proposed a prediction model for first-year growth response in prepubertal GHD children using auxological criteria, peak GH values in GH stimulation tests and height velocity (HV) response. The data analysis suggested that the first year HV was negatively correlated with age and height standard deviation score (HSDS) and positively correlated with birth weight, weight at beginning of therapy, GH dose, frequency of injection, target HSDS, and the peak GH response to a stimulation test. Cole et al. (Arch Dis Child 2004; 89:1024-1027) reported that GH stimulation test result, although not a gold standard for diagnosis, is a valuable predictor of growth in the first year of treatment. Blethen et al (J Clin Endocrinol Metab 1993; 76 (3):574-579) reported that the initial response to GH therapy may be predicted by age, degree of GHD, weight adjusted for height, GH dose, injection frequency, and mid-parental height. The Ranke model was extended to examine second-, third- and fourth-year growth response, and has demonstrated that first-year height velocity is the most important predictor of subsequent growth. Overall, the model could explain 61% of the growth response variability during the first year of GH treatment. A similar model, based on auxological parameters, could explain 46% of the growth response to GH treatment in subjects with TS (Ranke et al. J Clin Endocrinol Metab 2000; 85 (11):4212-4218).

Growth prediction models have variable predictive power, and although suitable to describe the variance within a defined cohort of patients, they fail to explain the total variance of the GH response. The major contributors to the remaining variance are conceivably genetic determinants.

There is thus a need to define a set of biological markers and genetic/genomic markers associated with short term GH treatment response that could complement the previously identified parameters to increase the accuracy with which response to GH treatment could be predicted.

SUMMARY OF THE INVENTION

According to one aspect of the invention, a method is provided for predicting the level of response after one month of treatment with growth hormone in an individual suffering from Growth Hormone Deficiency or Turner Syndrome by use of biological and genetic markers.

According to another aspect of the invention, a method is provided for predicting Growth Hormone Deficiency or Turner Syndrome treatment response after one month with growth hormone and, based on the prediction, optimizing the Growth Hormone Deficiency or Turner Syndrome patient treatment depending on the predicted clinical response.

DETAILED DESCRIPTION OF THE INVENTION

The present invention provides novel approaches to predicting the response to growth hormone (GH) treatment in individuals having Idiopathic Growth Hormone Deficiency (GHD) or Turner Syndrome (TS), thereby enabling the adjustment of the necessary dose of GH in a patient individualized manner.

Current medications to stimulate linear growth with GH in GHD and TS include SAIZEN®. The active ingredient of SAIZEN® is somatropin, a recombinant human growth hormone (r-hGH) produced by genetically engineered mammalian cells (mouse C127). Somatropin is a single-chain, non-glycosylated protein of 191 amino acids with two disulphide bridges.

SAIZEN® is registered in many regions in the following paediatric indications:
growth failure in children caused by decreased or absent secretion of endogenous growth hormone (GHD)
growth failure in children due to causes other than GHD (Turner Syndrome, growth disturbance in short children born SGA)
growth failure in prepubertal children due to chronic renal failure.

SAIZEN® is also registered in 42 countries, including 15 European countries and Switzerland, in the indication of "pronounced growth hormone deficiency" in the adult.

The term "growth hormone (GH)", as used herein, is intended to include growth hormone in particular of human origin, as obtained by isolation from biological fluids or as obtained by DNA recombinant techniques from prokaryotic or eukaryotic host cells, as well as its salts, functional derivatives, variants, analogs and active fragments.

GH is a hormone with pleiotropic effects that result from the complex mechanisms regulating its synthesis and secretion as well as from the GH downstream effects resulting in the activation or inhibition of a variety of different intracellular signaling pathways, responsible for different biological effects-of GH. At the cellular level, GH binds to one single receptor, but activates multiple responses within individual target cells. GH-responsive genes include IGF-I which is the major mediator of GH action on somatic growth, and also other proteins involved in the regulation of the metabolic effects of GH. Upon administration of exogenous GH, the effects on somatic growth are long-term, but in the short term they can be evaluated by a variety of markers in peripheral blood that reflect the onset of its biological action.

Recombinant human growth hormone can typically be administered to children in a daily dosage ranging from about 0.02 mg/kg/d of body weight up to about 0.07 mg/kg/d of body weight. This dosage may be given daily or accumulated as weekly dose, or the accumulated weekly dose be split into 3 or 6 equal doses per week.

The response to GH treatment, short-term as well as long-term, displays considerable inter individual variability. This is particularly evident for the endpoint of paediatric GH administration, i.e. the growth response, which varies significantly between subjects with TS but is also pronounced between children who are affected by GHD.

This variability can be investigated at two different levels. First, at the biological marker level, by assessing the individual growth response to GH administration by means of the biological markers of GH action commonly used in the clinical management of short stature subjects, as described more in detail below. Secondly, at the genotype level, which can be investigated by identifying the genetic factors responsible for the variation of biological markers associated to the response to GH intervention.

Existing clinical growth prediction models attempt to predict the individual response to GH treatment based on either pre-treatment characteristics and/or on clinical response after a short period of GH administration in comparison to the group response. Pre-treatment parameters used in existing prediction models for idiopathic GHD and Turner Syndrome children receiving GH therapy include auxological criteria such as height at baseline, mid-parental height, birth weight, birth length, height velocity etc., indices of endogenous GH secretion, biological markers of GH action such as insulin-like growth factors (IGF) and their binding proteins (IGFBP), and bone turnover markers.

The existing clinical growth prediction models have variable predictive power, and although suitable to describe the variance within a defined cohort of patients, they fail to explain the total variance of the GH response. The major contributors to the remaining variance are conceivably genetic determinants.

In recent years pharmacogenomics—inclusive of pharmacogenetics, as described in the present patent application—(PGx) has come into focus of physicians. Pharmacogenetics can be viewed as the study of inter-individual variations in DNA sequence as related to drug response. In this context the genome of an individual is analyzed leading to the description of genetic markers or susceptibility alterations of significance in this regard.

According to the present invention, the variability of the GH response was assessed by measuring biological markers of growth hormone action and by detecting genetic determinants potentially linked with early changes in IGF-I levels in GH-treated GHD and TS children and changes in IGFBP3 levels in TS children. This approach is of relevance not only in evaluating the efficacy response to GH treatment but also the treatment's safety profile and potentially long-term consequences. It has been documented that potential side effects of GH treatment include changes in insulin insensitivity and thus the development of impaired glucose tolerance, which can be monitored and depicted by standard clinical and laboratory measures. Within this context, the identification of the biological markers and genetic determinants will allow prediction of individual response to GH administration and thus stratify the patients for drug administration.

In this study, components of the IGF system, including IGF binding proteins, have been selected as primary efficacy markers. IGF-I is the most commonly used biochemical efficacy marker of GH exposure (De Boer H et al., J Clin Endocrinol Metab 1996; 81 (4):1371-1377). The GH-induced induction of IGF-I is rapid and reaches its maximum within a few weeks of GH administration.

Many effects of GH are mediated indirectly through IGF-I, which is produced mainly in the liver. There are six known IGF binding proteins, of which IGFBP3 is the most abundant in the circulation and accounts for 80% of all IGF binding. Levels of both IGF-I and IGFBP3 are strongly dependent on GH levels; thus, in GHD both measures are low. IGF-I and IGFBP3 are not independent of each other—they usually show a relationship, which is particularly close in children.

IGF-I levels vary to a larger extent with either endogenous or exogenous GH than IGFBP3 levels, which are more stable over time. A low pre-treatment IGF-I or IGFBP3 serum concentration or standard deviation score (SDS) predicts a good response during the first year of treatment in children with GHD, whereas normal levels may predict a less favourable growth response (Kristrom B et al., J Clin Endocrinol Metab 1997; 82 (9):2889-2898). The early changes in IGF-I and in its binding proteins (IGFBP3) under GH treatment have been shown to correlate with baseline levels and auxological status, endogenous GH secretion, GH dose and the initial growth velocity response.

IGF-I and IGFBP3 are called herein efficacy markers.

In the current settings, the IGF-I SDS levels and IGFBP3 SDS levels are evaluated between baseline, briefly before the initiation of GH treatment, and after 1 month of GH treatment.

To understand the genetic factors that underlie heritable diseases or the response to pharmacological treatment, classical genetics examines a single gene or a group of a few genes of interest in relation to the trait associated to the heritable diseases or the response to pharmacological treatment. Genomics, on the other hand, allows performance of this search for genetic determinants that result in particular phenotypic characteristics at the level of the entire genome. In the present study, the following genomic techniques were used:

Genotyping: through the identification of DNA variations, this method was used to detect genetic determinants in candidate genes that are potentially linked with GHD, TS or different response rates to GH treatment in these two diseases. The search for DNA variants was performed using single nucleotide polymorphisms (SNPs) as genetic markers. A SNP is a DNA locus at which the DNA sequence of two individuals carrying distinct alleles differs by one single nucleotide.

SNPs are the most common human genetic polymorphisms and their density on the genome is very high. Nearly 1.8 million SNPs have been discovered and characterized so far and are publicly available in several major databases (Worldwide Website: hapmap.org, October 2004). Identification of the SNPs of interest according to this invention can be performed with a method developed by Affymetrix or a comparable technique (Matsuzaki H et al., Genome Research 2004; 14:414-425). An association between the presence or the absence of a genetic marker (or a set of genetic markers called a haplotype) and a disease or response to treatment (the phenotype) indicates that a disease- or response-susceptibility gene may lie in the vicinity of the marker. This association is detected as a significant difference in the frequency of a particular allele at an SNP locus (or the difference in frequency of a haplotype) between patient groups with different phenotypes. This association can be detected either considering the heterozygote and homozygote status of the alleles for a given SNP, the so-called genotypic association, or on the basis of the presence of one or the other of the allele for a given SNP, the so-called allelic association. These association analyses are carried out with non parametric statistical methods, the Krustal Wallis test for genotypic and the Mann Whitney exact test for allelic.

Once a SNP has been found to be associated to a disease or response to treatment, categorical predictive analysis is required to further determine which allele is best associated to the response to treatment, and thus could serve as a predictive marker. This categorical analysis is carried out with Fisher exact test to examine the significance of the association between two variables, the response (low or high) and the genotype, in a 2×2 contingency table. In a further validation of these findings, the intermediate population is integrated and the tests are rerun this time in a 2×3 contingency table.

Moreover, predictive genetic markers are selected based on a Fisher p value less than 5% and a specificity threshold above 80%. Genetic allele frequency in the study population must be above 10%.

Exact Odds ratio together with the associated confidence interval indicated in brackets are reported as well as the predictive positive values.

Combination of 2 individual stratification genetic markers was also considered either through the "and" term or through the "or" term, this or going along the line of Boolean logic, namely requiring that either marker or both markers are present.

Complementary categorical analyses are performed for significant markers, considering the overall population, defined by three groups: Low responders, High responders, and Intermediate group (being neither Low nor High).

The terms "trait" and "phenotype" may be used interchangeably and refer to any clinically distinguishable, detectable or otherwise measurable property of an organism such as symptoms of, or susceptibility to a disease for example. Typically the terms "trait" or "phenotype" are used to refer to symptoms of, or susceptibility to GHD or TS; or to refer to an individual's response to a drug acting against GHD or TS.

As used herein, the term "allele" refers to one of the variant forms of a biallelic or multiallelic alteration, differing from other forms in its nucleotide sequence. Typically the most frequent identified allele is designated as the major allele whereas the other allele(s) are designated as minor allele(s). Diploid organisms may be homozygous or heterozygous for an allelic form.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A polymorphism may comprise a substitution, deletion or insertion of one or more nucleotides. A "single nucleotide polymorphism" (SNP) is a single base pair change. Typically a single nucleotide polymorphism is the replacement of one nucleotide by another nucleotide at the polymorphic site.

As will be discussed below in more details, the alteration ("susceptibility alteration") in a gene or polypeptide according to the invention may be any nucleotide or amino acid alteration associated to the response to growth hormone (GH) treatment in GHD or TS children.

An allelic marker is defined as a marker wherein the major allele is present either homozygously or heterozygously.

A genotypic marker is defined by an association between response and at least one of the three possible genotypes, homozygous for the major allele, homozygous for the minor allele or heterozygous.

Markers are selected based on continuous genetic analyses in the whole study population separated in a GHD population and a TS population.

A susceptibility may be any form of mutation(s), deletion(s), rearrangement(s) and/or insertion(s) in the coding and/or non-coding region of the gene, either isolated or in various combination(s). Mutations more specifically include point mutations. Deletions may encompass any region of one or more residues in a coding or non-coding portion of the gene. Typical deletions affect small regions, such as domains (introns) or repeated sequences or fragments of less than about 50 consecutive base pairs, although larger deletions may occur as well. Insertions may encompass the addition of one or several residues in a coding or non-coding portion of the gene. Insertions may typically comprise an addition of between 1 and 50 base pairs in the gene. Rearrangements include for instance sequence inversions. An alteration may also be an aberrant modification of the polynucleotide sequence, and may be silent (i.e., create no modification in the amino acid sequence of the protein), or may result, for instance, in amino acid substitutions, frameshift mutations, stop codons, RNA splicing, e.g. the presence of a non-wild type splicing pattern of a messenger RNA transcript, or RNA or protein instability or a non-wild type level of the polypeptide. Also, the alteration may result in the production of a polypeptide with altered function or stability, or cause a reduction or increase in protein expression levels.

Typical susceptibility alterations or genetic markers are single nucleotide polymorphisms (SNPs) as described above.

The presence of an alteration in a gene may be detected by any technique known per se to the skilled artisan, including sequencing, pyrosequencing, selective hybridisation, selective amplification and/or mass spectrometry including matrix-assisted laser desorption/ionization time-of-flight mass spectrometry (MALDI-TOF MS). In a particular embodiment, the alteration is detected by selective nucleic acid amplification using one or several specific primers. The alteration is detected by selective hybridization using one or several specific probes.

Further techniques include gel electrophoresis-based genotyping methods such as PCR coupled with restriction fragment length polymorphism (RFLP) analysis, multiplex PCR, oligonucleotide ligation assay, and minisequencing; fluorescent dye-based genotyping technologies such as oligonucleotide ligation assay, pyrosequencing, single-base extension with fluorescence detection, homogeneous solution hybridization such as TaqMan, and molecular beacon genotyping; rolling circle amplification and Invader assays as well as DNA chip-based microarray and mass spectrometry genotyping technologies.

Protein expression analysis methods are known in the art and include 2-dimensional gel-electrophoresis, mass spectrometry and antibody microarrays.

Sequencing can be carried out using techniques well known in the art, e.g. using automatic sequencers. The sequencing may be performed on the complete gene or, more preferably, on specific domains thereof, typically those known or suspected to carry deleterious mutations or other alterations.

Amplification may be performed according to various techniques known in the art, such as by polymerase chain reaction (PCR), ligase chain reaction (LCR) and strand displacement amplification (SDA). These techniques can be performed using commercially available reagents and protocols. A preferred technique is allele-specific PCR.

The term "gene" as used herein shall be construed to include any type of coding nucleic acid region, including genomic DNA (gDNA), complementary DNA (cDNA), synthetic or semi-synthetic DNA, any form of corresponding RNA (e.g., mRNA), etc., as well as non coding sequences, such as introns, 5'- or 3'-untranslated sequences or regulatory sequences (e.g., promoter or enhancer), etc. The term gene particularly includes recombinant nucleic acids, i.e., any non naturally occurring nucleic acid molecule created artificially, e.g., by assembling, cutting, ligating or amplifying sequences. A gene is typically double-stranded, although other forms may be contemplated, such as single-stranded. Genes may be obtained from various sources and according to various techniques known in the art, such as by screening DNA libraries or by amplification from various natural sources. Recombinant nucleic acids may be prepared by conventional techniques, including chemical synthesis, genetic engineering, enzymatic techniques, or a combination thereof. The term "gene" may comprise any and all splicing variants of said gene.

The term "polypeptide" designates, within the context of this invention, a polymer of amino acids without regard to the length of the polymer; thus, peptides, oligopeptides, and proteins are included within the definition of polypeptide. A fragment of a polypeptide designates any portion of at least 8 consecutive amino acids of a sequence of said protein, preferably of at least about 15, more preferably of at least about 20, further preferably of at least 50, 100, 250, 300 or 350 amino acids. This term also includes post-translational or post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides variants which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "treat" or "treating" as used herein is meant to ameliorate, alleviate symptoms, eliminate the causation of the symptoms either on a temporary or permanent basis, or to prevent or slow the appearance of symptoms of the named disorder or condition. The term "treatment" as used herein also encompasses the term "prevention of the disorder", which is, e.g., manifested by delaying the onset of the symptoms of the disorder to a medically significant extent. Treatment of the disorder is, e.g., manifested by a decrease in the symptoms associated with the disorder or an amelioration of the reoccurrence of the symptoms of the disorder.

"Response" to growth hormone treatment in an individual suffering from GHD or TS in the sense of the present invention is understood to be residual disease activity upon growth hormone treatment. More specifically the residual disease activity is herein associated to changes in biomarkers as a function of GH administration to these individuals suffering from GHD or TS.

Low responders according to the present invention show a response of low magnitude in IGF-I level or IGFBP-3 level (below the $25^{th}$ percentile) change between baseline and 1 month. High responders according to the present invention show a response of high magnitude in IGF-I level or IGFBP-3 level (above the $75^{th}$ percentile) change between baseline and after short-term treatment (e.g. 1 month).

"High responders" refers to those individuals who can be identified to show improved response to growth hormone treatment in comparison to the GHD or TS population who exhibit an average response level upon growth hormone treatment. The "high response" is exhibited by reduced residual disease activity. More specifically the residual disease activity in "high responders" is herein associated to changes in biomarkers as a function of GH administration to these individuals suffering from GHD or TS.

"Low responders" refers to those individuals who can be identified to show impaired response to growth hormone treatment in comparison to the GHD or TS population who exhibit an average response level upon growth hormone treatment. The "low response" is exhibited by increased residual disease activity. More specifically the residual disease activity in "low responders" is herein associated to changes in biomarkers as a function of GH administration to these individuals suffering from GHD or TS.

The present invention stems from the pharmacogenomics analysis evaluating gene variations in a group of 310 GHD and TS patients.

In the specific examples as disclosed in the present patent application, extreme categories required for categorical genetic analyses are defined by quartiles:
the low responders are herein represented by the first and lower quartile (designated as Q1) also designated by the lowest 25% of the data (25th percentile);
the high responders are herein represented by the third quartile and upper quartile (designated as Q3) also designated by the highest 75% (75th percentile);
the intermediate group is herein represented as the data from >Q1 and <Q3 also designated as the intermediary 50% of the data
in GHD and TS. In the below, the Odds Ratio (OR) describe the difference between extremes categories (Q1 and Q3); unless otherwise specified.

The cut-off values to define low and high response were:
In GHD: Low: <0.81 IGF-I SDS level change at one month
High: >1.91 IGF-I SDS level change at one month
In TS: Low: <1.15 IGF-I SDS level change at one month
High: >2.63 IGF-I SDS level change at one month IGF-I SDS in GHD The results of the study according to the invention show for the GHD population that the IGF-I level after one month of growth hormone treatment may be predicted based on the IGF-I SDS at treatment baseline, the treatment adherence in percent of expected doses/planned doses during the first month of treatment, the weight SDS at treatment baseline, the average growth hormone dose prescribed in µg/kg bodyweight/day and the age in years.

The response level after one month of growth hormone treatment is expressed in this embodiment as predicted IGF-I standard deviation score (SDS) after one month. IGF-I SDS is an efficacy marker for growth response.

Baseline according to this invention is defined as the patient's clinical and biological characteristics before treatment initiation.

The predicted IGF-I SDS after one months of growth hormone treatment is abbreviated herein as IGF-I_SDS__1M.

The IGF-I SDS at treatment baseline is abbreviated herein as IGF-I_SDS_B, and further defined in Table 1 below.

The treatment adherence in percent of expected doses/planned doses during the first month of treatment is abbreviated herein as adherence. Adherence is set at the beginning of the treatment by the physician. It is further defined in Table 1 below.

The weight SDS at treatment baseline is abbreviated herein as bl_wt SDS and is defined in kg. It is further defined in Table 1 below.

The average growth hormone dose prescribed in µg/kg bodyweight/day is abbreviated herein as dose. The dose is prescribed by the physician treating the individual according to the approved dose in countries participating to the study.

The chronological age in years is abbreviated herein as age and further defined in Table 1 below.

The present invention is thus directed in a first embodiment to a method of predicting the level of response to treatment with growth hormone in an individual having Growth Hormone Deficiency (GHD), the method comprising the steps of:
a. identifying IGF-I SDS at treatment baseline ("IGF-I_SDS_B");
b. setting the treatment adherence in percent of expected doses/planned doses during the first month of treatment ("adherence");
c. measuring the weight SDS at treatment baseline ("bl_wt SDS");
d. setting the average growth hormone dose prescribed in µg/kg bodyweight/day ("dose");
e. providing the age in years ("age"); and
f. calculating the predicted IGF-I SDS after one month of treatment with growth hormone as IGF-I_SDS__1M=−constant+(a×IGF-I_SDS_B)+(c×"adherence")+(b×bl_wt SDS)+(e×"dose")+(d×"age"), wherein a, b, c, d and e are positive coefficients.

In a preferred embodiment, the present invention is directed to a method of predicting the level of response to treatment with growth hormone in an individual having Growth Hormone Deficiency (GHD), the method comprising the steps of:
a. identifying IGF-I SDS at treatment baseline ("IGF-I_SDS_B");
b. setting the treatment adherence in percent of expected doses/planned doses during the first month of treatment ("adherence");
c. measuring the weight SDS at treatment baseline ("bl_wt SDS");
d. setting the average growth hormone dose prescribed in µg/kg bodyweight/day ("dose");
e. providing the age in years ("age"); and
f. calculating the predicted IGF-I SDS after one month of treatment with growth hormone as IGF-I_SDS__1M=−4.7265+(0.7065×IGF-I_SDS_B)+(0.0423×"adherence")+(0.2446×bl_wt SDS)+(0.0402×"dose")+(0.057×"age").

Preferably, this method is directed at predicting the level of response after 1 month of treatment with growth hormone. The method is preferably directed at predicting IGF-I SDS after one month of treatment with growth hormone.

Preferably, the method according to the invention does not include an invasive step on the individual's body.

The method of prediction defined above accounts for 66% of the variability (adjusted $R^2$) in IGF-I SDS at 1 month; excluding three outliers gave an adjusted $R^2$ of 76%.

Genomic Markers

In patients with the genotype AA in CDK4_rs2270777 the method of prediction accounts for 81% of the variability on IGF-I SDS at 1 month.

In patients with the allele A in LEPR_rs970467 the method of prediction accounts for 71% of the variability on IGF-I SDS at 1 month.

IGF-I SDS in TS

The results of the studies according to the invention also show for the TS population that IGF-I level after one month of growth hormone treatment may be predicted based on the IGF-I SDS at treatment baseline, the concentration of fasting triglycerides at baseline in mmol/L, the weight SDS of the individual at birth, the weight SDS at treatment baseline, the presence or absence of thyroid therapy and the average growth hormone dose prescribed in µg/kg bodyweight/day.

The response level after one month of growth hormone treatment is expressed in this embodiment as predicted IGF-I standard deviation score (SDS) after one month. IGF-I SDS is an efficacy marker for growth response.

The predicted IGF-I SDS after one month of growth hormone treatment is abbreviated herein as IGF-I_SDS_1M.

The IGF-I SDS at treatment baseline is abbreviated herein as IGF-I_SDS_B as described above.

The concentration of fasting triglycerides at baseline in mmol/L is abbreviated herein as Triglycerides. Fasting triglyceride levels are measured after a few hours of fasting, usually after 4-12 hours of fasting, preferably after 8-12 hours of fasting.

The weight SDS at birth is abbreviated herein as birth_wt SDS and is further defined in Table 1.

The weight SDS at treatment baseline is abbreviated herein as bl_wt SDS as described above.

Thyroid therapy is abbreviated herein as HORM-REPL and means that the patient is on stable thyroid replacement therapy for hyperthyroidism during the growth hormone therapy. If thyroid therapy is planned during the growth hormone therapy, the value of HORM REPL is 1. If no thyroid therapy is planned during growth hormone therapy the value of HORM REPL is 0.

The average growth hormone dose prescribed in µg/kg bodyweight/day is abbreviated herein as dose as described above.

The present invention is thus directed in a second embodiment to a method of predicting the level of response to treatment with growth hormone in an individual having Turner Syndrome (TS), the method comprising the steps of:
a. identifying IGF-I SDS at treatment baseline ("IGF-I_SDS_B");
b. measuring the concentration of fasting triglycerides at baseline in mmol/L ("Triglycerides");
c. providing the weight SDS at birth ("birth_wt SDS);
d. measuring the weight SDS at treatment baseline ("bl_wt SDS");
e. identifying the presence or absence of thyroid therapy ("HORM-REPL"), wherein HORM REPL is 1 if thyroid therapy is planned in the individual during growth hormone treatment and wherein "HORM REPL" is 0 if no thyroid therapy is planned during growth hormone therapy;
f. setting the average growth hormone dose prescribed in µg/kg bodyweight/day ("dose"); and
g. calculating the predicted IGF-I SDS after one month of treatment with growth hormone as IGF-I_SDS_1M=constant+(a×IGF-I_SDS_B)−(e×Triglycerides)−(f×birth_wt SDS)+(b×bl_wt SDS)−(d×HORM REPL)+(c×dose), wherein a, b, c, d, e and f are positive coefficients.

In a preferred embodiment, the present invention is directed to a method of predicting the level of response to treatment with growth hormone in an individual having Turner Syndrome (TS), the method comprising the steps of:
a. identifying IGF-I SDS at treatment baseline ("IGF-I_SDS_B");
b. measuring the concentration of fasting triglycerides at baseline in mmol/L ("Triglycerides");
c. providing the weight SDS at birth ("birth_wt SDS);
d. measuring the weight SDS at treatment baseline ("bl_wt SDS");
e. identifying the presence or absence of thyroid therapy ("HORM-REPL"), wherein HORM REPL is 1 if thyroid therapy is planned in the individual during growth hormone treatment and wherein "HORM REPL" is 0 if no thyroid therapy is planned during growth hormone therapy;
f. setting the average growth hormone dose prescribed in µg/kg bodyweight/day ("dose"); and
g. calculating the predicted IGF-I SDS after one month of treatment with growth hormone as IGF-I_SDS_1M=0.0995+(0.4371×IGF-I_SDS_B)−(0.3007×Triglycerides)−(0.0695×birth_wt SDS)+(0.3661×bl_wt SDS)−(0.6797×HORM REPL)+(0.308×dose).

Preferably, this method is directed at predicting the level of response after 1 month of treatment with growth hormone. The method is preferably directed at predicting IGF-I SDS after one month of treatment with growth hormone.

Preferably, the method according to the invention does not include an invasive step on the individual's body.

The method of prediction defined above accounts for 47% of the variability (adjusted $R^2$) in IGF-I SDS at 1 month; excluding one outlier produced an adjusted $R^2$ of 53%.

Genomic Markers

In patients with the allele C in SH2B2_rs2906713 the method of prediction accounts for 56% of the variability on IGF-I SDS at 1 month.

In patients with the genotype AA in PIK3CB_rs10513055 the method of prediction accounts for 57% of the variability on IGF-I SDS at 1 month.

In patients with the allele A in CDK4_rs2069502 the method of prediction accounts for 57% of the variability on IGF-I SDS at 1 month.

In patients with the allele G in CDK4_rs2270777 the method of prediction accounts for 56% of the variability on IGF-I SDS at 1 month.

In patients with the genotype GG in BCL2_rs4456611 or the allele C in SH2B2 rs2906713 the method of prediction accounts for 59% of the variability on IGF-I SDS at 1 month.

In patients with the allele A in BCL2_rs4456611 and the genotype AA in PIK3CB_rs10513055 the method of prediction accounts for 56% of the variability on IGF-I SDS at 1 month.

In patients with the allele A in BCL2_rs4456611 and the allele A in CDK4_rs2069502 the method of prediction accounts for 57% of the variability on IGF-I SDS at 1 month.

Karyotype

In patients with the Karyotype 45X presence the method of prediction accounts for 61% of the variability on IGF-I SDS at 1 month.

IGFBP3 in TS

The results of the study according to the invention also show for the TS population that the IGFBP3 level after one month of growth hormone treatment may be predicted based on the IGFBP3 SDS at treatment baseline, the concentration of fasting triglycerides at baseline in mmol/L, the concentration of TSH (Thyroid stimulating hormone) at baseline in mIU/L, the age at baseline in years, the weight SDS at treatment baseline, and the average growth hormone dose prescribed in µg/kg bodyweight/day.

The response level after one month of growth hormone treatment is expressed in this embodiment as predicted IGFBP3 standard deviation score (SDS) after one month. IGFBP3 SDS is an efficacy marker for growth response.

The predicted IGFBP3 SDS after one month of growth hormone treatment is abbreviated herein as IGFBP3_SDS_1M.

The IGFBP3 SDS at treatment baseline is abbreviated herein as IGFBP3_SDS_B and is further defined in Table 1.

The concentration of fasting triglycerides at baseline in mmol/L is abbreviated herein as Triglycerides. Fasting triglyceride levels are measured after a few hours of fasting, usually after 4-12 hours of fasting, preferably after 8-12 hours of fasting.

The concentration of TSH at baseline in mIU/L is abbreviated as TSH_B.

The age in years is abbreviated herein as age as described above.

The weight SDS at treatment baseline is abbreviated herein as bl_wt SDS as described above.

The average growth hormone dose prescribed in µg/kg bodyweight/day is abbreviated herein as dose as described above.

The present invention is thus directed in a third embodiment to a method of predicting the level of response to treatment with growth hormone in an individual having Turner Syndrome (TS), the method comprising the steps of:
a. identifying IGFBP3 SDS at baseline ("IGFBP3_SDS_B");
b. measuring the concentration of fasting triglycerides at baseline in mmol/L ("Triglycerides");
c. measuring the concentration of TSH at baseline in mIU/L ("TSH_B");
d. providing the age at baseline in years ("age");
e. providing the weight SDS at treatment baseline ("bl_wt SDS");
f. setting the average growth hormone dose prescribed in µg/kg bodyweight/day ("dose"); and
g. calculating the predicted IGFBP3 SDS after one month of treatment with growth hormone as IGFBP3_SDS_1M=constant+(a×IGFBP3_SDS_B)−(d×Triglycerides)+(e×TSH_B)−(b×age)+(c×bl_wt SDS)+(f×dose), wherein a, b, c, d, e and f are positive coefficients.

In a preferred embodiment, the present invention is directed to a method of predicting the level of response to treatment with growth hormone in an individual having Turner Syndrome (TS), the method comprising the steps of:
a. identifying IGFBP3 SDS at baseline ("IGFBP3_SDS_B");
b. measuring the concentration of fasting triglycerides at baseline in mmol/L ("Triglycerides");
c. measuring the concentration of TSH at baseline in mIU/L ("TSH_B");
d. providing the age at baseline in years ("age");
e. providing the weight SDS at treatment baseline ("bl_wt SDS");
f. setting the average growth hormone dose prescribed in µg/kg bodyweight/day ("dose"); and
g. calculating the predicted IGFBP3 SDS after one month of treatment with growth hormone as IGFBP3_SDS_1M=1.176+(0.4658×IGFBP3_SDS_B)−(0.182×Triglycerides)+(0.0215×TSH_B)−(0.0497×age)+(0.0897×bl_wt SDS)+(0.0032×dose).

Preferably, this method is directed at predicting the level of response after 1 month of treatment with growth hormone. The method is preferably directed at predicting IGFBP3 SDS after one month of treatment with growth hormone.

Preferably, the method according to the invention does not include an invasive step on the individual's body.

The method of prediction defined above accounts for 53% of the variability (adjusted $R^2$) in IGFBP3 SDS at 1 month; excluding two outliers increased the $R^2$ to 56%.

Genomic Markers

In patients with the allele C in SH2B2_rs2906713 the method of prediction accounts for 66% of the variability on IGFBP3 SDS at 1 month.

In patients with the genotype AA in PIK3CB_rs10513055 the method of prediction accounts for 60% of the variability on IGFBP3 SDS at 1 month.

In patients with the genotype GG in BCL2_rs4456611 or the allele C in SH2B2 rs2906713 the method of prediction accounts for 64% of the variability on IGFBP3 SDS at 1 month.

In patients with the allele A in BCL2_rs4456611 and the genotype AA in PIK3CB_rs10513055 the method of prediction accounts for 60% of the variability on IGFBP3 SDS at 1 month.

In patients with the allele A in BCL2_rs4456611 and the allele A in CDK4_rs2069502 the method of prediction accounts for 64% of the variability on IGFBP3 SDS at 1 month.

Karyotypes

In patients without the Karyotype 45X the method of prediction accounts for 58% of the variability on IGFBP3 SDS at 1 month. Karyotype 45X means the presence of 45 chromosomes in each cell rather than 46. The missing chromosome is an X-chromosome.

In patients without the Karyotype i(Xq) presence the method of prediction accounts for 59% of the variability on IGFBP3 SDS at 1 month. Karyotype i(Xq) defines the presence of an isochromosome of the long arm of one X chromosome.

The results according to this invention may be applied in approaches of personalized medicine. Personalized medicine is, according to the present patent application, the use of information and data from a patient's biological markers and genotype to stratify disease, select a medication, provide a therapy, or initiate a preventative measure that is particularly suited to that patient at the time of administration. It is believed that personalized medicine will make it possible in the future to give the appropriate drug, at the appropriate dose, to the appropriate patient, at the appropriate time.

Patients with a genotype predictive of a high response can be given the standard dose of GH, i.e. the dose currently used in clinical practice, which is for children a daily dosage ranging from about 0.02 mg/kg of body weight up to about 0.07 mg/kg of body weight. Alternatively these patients can be given an optimized dose.

Patients with markers predictive of a low response can be treated with growth hormone according to an optimized adherence and therapy plan. Thus, adherence may be improved and/or the dose of GH may be optimized. An optimized dose of GH to be given to a low responder may be an increased dose of GH compared to the standard dose as a dose-response relationship in terms of height velocity in the first 2 years of treatment has been demonstrated; and this in a dose range compatible with the fixed dose used to treat GHD or TS patients in the current settings. Low responders can also be candidate patients for therapies with long acting analogues of GH with a frequency of administration which is decreased.

In a further embodiment the present invention is thus directed to a method wherein an individual identified as low responder or high responder is treated with growth hormone according to an optimized adherence and therapy plan.

The invention is thus directed to a method for treating Growth Hormone Deficiency (GHD) or Turner Syndrome (TS) in an individual in need thereof, the method comprising the steps of:
a. identifying the level of response to treatment with growth hormone according to any of the methods described above,
b. treating the individual according to an optimized adherence and therapy plan.

In a preferred embodiment, the individual is identified as low responder and is treated with a dose of growth hormone that is optimized compared to the standard dose.

In one embodiment, a low responder is treated with a dose of growth hormone that is increased compared to the standard dose.

In a further embodiment, the invention relates to the use of growth hormone in the preparation of a medicament for treating Growth Hormone Deficiency (GHD) or Turner Syndrome (TS) in an individual in need thereof, wherein the individual has been identified according to any of the methods described above to be a low responder or a high responder to the treatment with growth hormone.

In a further embodiment, the present invention relates also to growth hormone for use in treating Growth Hormone Deficiency (GHD) or Turner Syndrome (TS) in an individual in need thereof, wherein the individual has been identified according to any of the methods described above to be a low responder or a high responder to the treatment with growth hormone.

In the method of predicting, or method of treating according to the invention the growth hormone is preferably human growth hormone and more preferably recombinant human growth hormone. Particular embodiments of the invention refer to growth hormone as sold under the tradename SAIZEN®.

Formulations useful in a method of treating a GHD or TS patient according to the invention may be a liquid pharmaceutical formulation comprising growth hormone or a reconstituted freeze-dried formulation comprising growth hormone. Preferably the formulation is stabilized by a polyol, more preferably a disaccharide and even more preferably sucrose.

In the following the present invention shall be illustrated by means of the following examples that are not to be construed as limiting the scope of the invention.

EXAMPLES

Example 1

Methods

Study Design

PREDICT (NCT00256126) was a Phase IV, open-label, prospective multicentre study in GH-treatment-naïve, prepubertal children with GHD or TS. The primary objective of the PREDICT study was to investigate which were the most responsive serum biomarkers after 1 month of treatment with recombinant human GH (r-hGH) in children with GHD or TS.

Patients

To be eligible for this study, children had to have a diagnosis of GHD or TS and have been a candidate for r-hGH therapy. For GHD the diagnosis was confirmed using two different GH stimulation tests (without priming); both tests required a peak GH concentration of ≤10 mcg/L against a GH international reference standard. For TS the diagnosis was confirmed by karyotype analysis. The presence of a 45X/46X or 45X cell line, or a cell line with deletion of the short arm of the X chromosome (SHOX or Xp deletion) was required. Children with SHOX deletions were classified as having TS if the deletion was proximal to the junction between Xp22.2 and Xp22.3.

Patients were excluded if they had GHD due to central nervous system tumor, trauma, infection, previous irradiation, or cranial surgery; or had received previous treatment with GH, GH-releasing hormone, anabolic steroids, or glucocorticoids (except for hormonal substitution if both the condition and regimen remained stable for at least 3 months). Patients with any severe associated pathology affecting growth, diabetes mellitus type I or II, or idiopathic intracranial hypertension were also excluded. Patients with significant concomitant illness, chronic kidney, liver or infectious disease, malignancy, or autoimmune disease (except chronic autoimmune thyroiditis with normal levels of thyroid hormones) were not eligible for this study.

All children needed to be GH treatment-naïve and have prepubertal status defined by Tanner stage 1. Normal thyroid function or adequate substitution for at least 3 months was required, as well as weight or stature within the population-specific normal ranges for gender (>$5^{th}$ and <$95^{th}$ percentiles).

Patients were recruited at paediatric endocrinology clinics. Before a child could participate in the study, his/her parent(s) or guardian(s) had to provide written informed consent. If the child was old enough to read and write, he/she was offered a separate assent form to sign. The informed consent process was in accordance with good clinical practice, local regulatory requirements and the guiding principles of the Declaration of Helsinki.

Treatment r-hGH (Saizen®, Merck Serono S,A.—Geneva, Switzerland) solution (8 mg/24 IU, containing 0.3% metacresol) was administered subcutaneously (sc) daily at bedtime using an auto-injector device (One.Click®, Merck Serono S.A.—Geneva) for 1 month. Children with GHD and TS received the once daily sc registered r-hGH dose (0.035 and 0.050 mg/kg/day body weight, respectively).

Outcomes

The primary endpoint was a within-patient change in the standard deviation score (SDS) for serum IGF-I after 1 month of r-hGH therapy greater than 0.31 SD in children with GHD or TS. The requirement for a change greater than 15% was based on both the intra and inter assay variability for IGF-I. Secondary endpoints included change in other GH dependent biomarkers: IGFBP3, fasting glucose, fasting insulin, insulin resistance index (homeostasis model assessment of insulin resistance, HOMA-IR test), total cholesterol, LDL-cholesterol, HDL-cholesterol, triglycerides, and bAP after 1 month of treatment. In addition free $T_4$, and thyroid stimulating hormone (TSH) were also assessed. Safety was assessed by reporting adverse events (AEs), routine hematology and biochemistry parameters, changes from baseline in glucose metabolism parameters, lipid levels, and thyroid function tests. Subsequent analyses included the correlation between the percentage change in biomarker levels and IGF-I SDS, IGFBP3 SDS or HOMA-IR.

At the baseline visit, demographic data (sex, age, gestational age at birth, birth length and weight, parental height), and medical history were collected. Body weight and height were measured and body mass index (BMI) calculated. Blood sampling for central analysis of serum biomarkers was performed at baseline and after 1 month of treatment. IGF-I and IGFBP3 were assayed using the Immulite 2000 Immunoassay analyzer (Siemens Healthcare Diagnostics, Germany).

Statistical Analyses

The sample size was based on the level of change in IGF-I SDS after 1 month of treatment for patients with TS as reported in a previous study (van Teunenbroek A et al., J Clin Endocrinol Metab 81:4013-4021). A sample size of 163 patients was required to provide 90% power to test the 0.025 one-sided level of significance for an increase of 15% in IGF-I levels from baseline to 1 month, as defined by mean (SD) baseline levels of 89.0 (37.2) µg/L (van Teunenbroek A et al., J Clin Endocrinol Metab 81:4013-4021; 1996). To allow for a 10% drop-out rate, 360 patients needed to be enrolled to ensure 326 evaluable patients with GHD or TS for analysis.

Height, weight, BMI, IGF-I and IGFBP3 levels were converted to SDS using relevant reference data. SDS for IGF-I and IGFBP3 were calculated taking into account mean levels and variability for age and gender based on reference data from a population of healthy children (Elmlinger M W et al., Clin Chem Lab Med 42:654-664; 2004). This provided contours of normal distributions fitted to the frequency of log-transformed serum levels, for 0 SD (i.e. mean), ±1 SD and ±2 SD. When no reference data were available, the change in concentration was normalized relative to baseline and expressed as a percentage.

Because the data were not normally distributed; the Wilcoxon signed-rank test was used to evaluate changes within the two groups, and the Wilcoxon rank sum test was used to evaluate changes between the two groups. Spearman's coefficient was used to measure the correlation between the percentage change in biomarker levels and IGF-I SDS, IGFBP3 SDS or HOMA-IR.

Prediction Model Development

Multivariate linear regression was used to find the best-fit model that predicted IGF-I SDS at 1 month for GHD and IGF-I SDS and IGFBP3 SDS at month 1 for TS. SAS® was used to conduct the analysis.

Potential predictive factors included birth, auxological, treatment and parental characteristics, and baseline biomarkers (see Table 1).

The stepwise procedure was used with relaxed requirements (a=0.15) to identify the strongest predictors (up to 10).

Akaike's Information Criteria (AIC), a tool for optimal model selection, is a function of the number of observations, the sum of squared errors and the number of predictors (Akaike H. 2nd International Symposium of Information Theory 1973. B N Petrov and F Caski, eds. Akademiai Kiado, Budapest, 267-281).

The model with the smallest AIC is considered as the best-fit model.

The term $R^2$ is the proportion of variability in the data set that is accounted for by the model and provides a measure of how well future outcomes are likely to be predicted by the model. Adjusted $R^2$ additionally takes into account the number of explanatory terms. The reported model includes received mean daily GH dose by kg body-weight (μg/kg) and balances AIC, adjusted $R^2$, and the number and clinical relevance of predictors for ease of use in a clinical setting.

The reported model was then applied in subgroup analyses of genomic markers showing the strongest associations with IGF-I SDS change to evaluate the variability explained in these subpopulations.

TABLE 1

Potential predictive factors under consideration.

| Potential predictive factor | Description |
|---|---|
| Birth characteristics | |
| Gestational age (weeks) | |
| Gender (for GHD) | |
| Height SDS at birth | In statistics, a standard deviation score is a dimensionless quantity derived by subtracting the population mean from an individual raw score and then dividing the difference by the population standard deviation. This conversion process is called standardizing or normalizing. For each subject, a standard deviation score (SDS) has been calculated for height at birth (cm). The reference data used to calculate height at birth SDS values have been published by Usher et al (J Pediatr 74, 901-910; 1969). |
| Weight SDS at birth | In statistics, a standard deviation score is a dimensionless quantity derived by subtracting the population mean from an individual raw score and then dividing the difference by the population standard deviation. This conversion process is called standardizing or normalizing. For each subject, a standard deviation score (SDS) has been calculated for weight at birth (kg). The reference data used to calculate weight at birth SDS values have been published by Usher et al (J Pediatr 74, 901-910; 1969). |
| Born SGA (Small for Gestational Age) | Height SDS at birth <= −2 and/or Weight SDS at birth <= −2 (Clayton et al., J. Clin Endocrinol Metabol 92:804-810; 2007) |
| Auxological characteristics | |
| Age at baseline (years) | Chronological age = {(Date of baseline assessment) − (Date of birth)}/365.25 Age is reported with one decimal point. |
| BMI SDS at baseline | In statistics, a standard deviation score is a dimensionless quantity derived by subtracting the population mean from an individual raw score and then dividing the difference by the population standard deviation. This conversion process is called standardizing or normalizing. For each subject, a standard deviation score (SDS) has been calculated for BMI at baseline (kg/m$^2$). The reference data used to calculate BMI at baseline SDS values have been published by Rolland-Cachera et al (Eur J Clin Nutr. 1991 January; 45(1):13-21). |
| Height SDS at baseline | In statistics, a standard deviation score is a dimensionless quantity derived by subtracting the population mean from an individual raw score and then dividing the difference by the population standard deviation. This conversion process is called standardizing or normalizing. For each subject, a standard deviation score (SDS) has been calculated for height at baseline (m). The reference data used to calculate height at baseline SDS values have been published by Sempé et al (Auxologie, methods et sequences. Paris: Theraplix, 1979). |
| Weight SDS at baseline | In statistics, a standard deviation score is a dimensionless quantity derived by subtracting the population mean from an individual raw score and then dividing the difference by the population standard deviation. This conversion process is called standardizing or normalizing. For each subject, a standard deviation score (SDS) has been calculated for height at baseline (kg). The reference data used to calculate height at baseline SDS values have been published by Sempé et al (Auxologie, methods et sequences. Paris: Theraplix, 1979). |
| Bone age (years) | A left wrist X-ray is required to establish bone age at baseline, if not performed within the last 6 months. The investigator according to the Greulich and Pyle method performs the evaluation, and the value is reported in years. |
| Bone age delay (years) | Chronological age (years) − Bone age (years) |
| Mid-parental height SDS | Mid-parental height (SDS): Mid-parental height (SDS) = (Mother's height (SDS) + Father's height (SDS)/1.61 (Ranke, Horm Res 45:64-66; 1996) |

TABLE 1-continued

Potential predictive factors under consideration.

| Potential predictive factor | Description |
|---|---|
| | Where, Mother's height (SDS) = (Mother's height (cm) − 163.3)/5.6 Father's height (SDS) = (Father's height (cm) − 175.0)/6.0. (Adult reference data, Sempe et al, 1979) |
| Distance to target height SDS | Height SDS at baseline − Mid-parental height SDS |
| GH treatment | |
| GH dose (µg/kg/day) | Dose was transformed from mg/kg/day to µg/kg/day |
| Adherence (%) | Each patient's study treatment adherence is estimated as a percentage of their target number of days they should have received one or more growth hormone injections whilst in the study (% adherence = 100 × number of days growth hormone injections were received/number of days on study) |
| Other treatment | |
| Thyroid replacement therapy | Reported as concomitant medications during the study. |
| GH Severity | |
| GH peak (µg/L) (for GHD) | Documented pre-established diagnosis of GHD with a GH peak response of <10 µg/L with 2 GH stimulation tests, without priming with oestradiol. |
| Biomarkers at baseline | |
| IGF-I SDS | Absolute concentration of IGF-I was converted to a standard deviation score (SDS) (see reference below). In statistics, a standard deviation score is a dimensionless quantity derived by subtracting the population mean from an individual raw score and then dividing the difference by the population standard deviation. This conversion process is called standardizing or normalizing. For each subject at and each timepoint, standard deviation scores (SDS) have been calculated for IGF-I. The reference data used to calculate SDS values have been published by Elmlinger et al (Clin Chem Lab Med 42(6):654-664; 2004). |
| IGFBP3 SDS | Absolute concentration of IGFBP3 was converted to a standard deviation score (SDS) (see reference below). In statistics, a standard deviation score is a dimensionless quantity derived by subtracting the population mean from an individual raw score and then dividing the difference by the population standard deviation. This conversion process is called standardizing or normalizing. For each subject at and each timepoint, standard deviation scores (SDS) have been calculated for IGFBP3. The reference data used to calculate SDS values have been published by Elmlinger et al (Clin Chem Lab Med 42(6):654-664; 2004). |
| HOMA-IR | Central laboratory reported. |
| Glucose (mmol/L) | Central laboratory reported. |
| Insulin (pmol/L) | Central laboratory reported. |
| Total cholesterol (mmol/L) | Central laboratory reported. |
| LDL-cholesterol (mmol/L) | Central laboratory reported. |
| HDL-cholesterol (mmol/L) | Central laboratory reported. |
| Triglycerides (mmol/L) | Central laboratory reported. |
| Bone alkaline phosphatase (U/L) | Central laboratory reported. |
| Free T4 (pmol/L) | Central laboratory reported. |
| TSH (mIU/L) | Central laboratory reported. |

BMI, body mass index;
GH, growth hormone;
HDL, high-density lipoprotein;
HOMA-IR, homeostasis model assessment of insulin resistance;
IGF, insulin-like growth factor;
IGFBP3, IGF binding protein 3;
LDL, low-density lipoprotein;
SDS, standard deviation score;
SGA, small for gestational age;
T4, thyroxine;
TSH, thyroid stimulating hormone.

Example 2

Results

Demographics

The study was carried out between May 2005 and September 2007 in 42 centres across 15 countries. These included several European countries as well as Argentina, Australia, Canada, Korea, Russia, and Taiwan. In all, 52.9% of the study population was enrolled in three countries: Russia 23.0% (73/318), Spain 15.4% (49/318), and France 14.5% (46/318). In total, 319 children agreed to participate in the study but one patient with GHD was withdrawn prior to receiving treatment. Therefore, 318 children were enrolled in the study and received at least one dose of r-hGH (the intention-to-treat population): of these, 169 had GHD and 149 had TS. In the GHD group, 63 were female. In total, 314 (98.7%) children completed the study. Four children were withdrawn from the study prematurely; the reasons for discontinuation were auto-injector defect (n=1), vomiting (n=1), withdrawal of consent (n=1), and lost to follow up (n=1). One or more major protocol deviations occurred in 11.3% (36/318) of patients (GHD, n=27; TS, n=9). The most common protocol deviations were weight for stature outside the protocol range (16/319), <80% of scheduled treatment administered (10/319) and less than 4/7 days dosage in the last week of treatment/week of sampling (5/319). Compliance with treatment was generally high (95%) and was similar in both groups. There were some interesting similarities between the groups in gestational age at birth, birth length, age, height, and height velocity. However the two groups differed slightly at baseline: the GHD group had a lower median BMI, higher birth weight, shorter parents, lower bone age, lower IGF-I and IGFBP3, higher cholesterol, LDL-cholesterol, and bAP, and lower T4, and TSH than the TS group. In the GHD group, IGF-I but not IGFBP3 was influenced by peak GH.

Of the children with TS, 46.3% (69/149) had monosomy X (45, X), consistent with known TS population norms (Sybert V P et al., N England J Med 351:1227-1238). The remainder had partial deletion (46, del[X]), an isochromosome of the long arm of one X chromosome (46, X i[Xq]), or mosaicism for 45 X with one or more cell lineages.

Safety

The safety profile of Saizen® in this study was consistent with prior experience with GH therapy. In one child with GHD, a serious AE of streptococcal tonsillitis was reported but this was considered to be unlikely to be related to treatment. There were few meaningful changes observed in hematology parameters, thyroid function tests, or vital signs over the course of the treatment period.

Biomarkers at Baseline

Significantly lower IGF-I and IGFBP3 values (both SDS and absolute values) were observed in the GHD group compared with the TS group as one would expect. Children with TS had significantly higher triglyceride levels compared with the GHD group, but total- and LDL-cholesterol levels were significantly lower. HDL-cholesterol levels did not differ significantly between the two groups. There were no significant differences in glucose metabolism biomarkers (insulin level, glucose level, and insulin resistance index) between the two groups. Although the BMI SDS was significantly higher in the TS group, the degree of insulin sensitivity did not differ significantly between the groups at baseline.

When children with GHD were categorized on the severity of GHD based on the peak GH level attained during the stimulation test, the majority (92%, 156/169) had GH levels≤7.0 µg/L (79 had <4, 77 had >4-7 and 13 had 7-10 µg/L).

Biomarker Changes after 1 Month of Treatment

The primary efficacy endpoint was met with a ≥0.31 increase in IGF-I SDS from baseline to 1 month in 92% of children with GHD or TS. After 1 month of treatment, there were statistically significant changes from baseline in the levels of all biomarkers measured in children with GHD or TS with the exception of the atherogenic index (LDL-cholesterol/HDL-cholesterol) in both GHD and TS children as well as TSH levels in GHD only. Considerable variability was observed in the magnitude of change in all biomarkers in both GHD and TS. When ranked by the magnitude of change from baseline after 1 month, IGF-I and fasting insulin levels ranked first and second, respectively, in both GHD or TS followed by IGFBP3. The first five most "sensitive" biomarkers were the same in both groups.

There were also significant differences in the degree of change in biomarkers between the groups. Children with TS showed significantly greater median increases in IGF-I SDS and IGF-I SDS/IGFBP3 SDS compared with children with GHD. In contrast, children with GHD showed significantly greater median decreases in total- and LDL-cholesterol, compared with children with TS. Changes in HDL-cholesterol, triglycerides, bAP, and insulin resistance did not significantly differ between the groups.

We observed a significant difference in IGF-I and IGFBP3 changes after 1 month of treatment among the three subgroups of GH deficiency according to GH peak at stimulation diagnosis test (peak<4, >4-7 and >7-10 µg/ml). Between group differences were p<0.001 for IGF-I and p<0.008 for IGFBP3. This finding is consistent with a difference in the severity of GH deficiency as classified by GH peak.

Correlation Analyses

Correlations between percentage changes from baseline in levels of biomarkers with changes in IGF-I SDS, IGFBP3 SDS, IGF-I SDS/IGFBP3 SDS or HOMA-IR after 1 month of GH treatment are shown in Table 4. In both groups changes in both insulin levels and HOMA insulin resistance index were significantly strongly correlated with changes in IGF-I SDS but not with change in IGFBP3; this is an interesting finding as changes in IGF-I and IGFBP3 are themselves correlated. Changes in all lipid biomarkers with the exception of triglycerides showed a statistically significant correlation with changes in IGFBP3 in the TS but not in the GHD group. Changes in IGF-I SDS/IGFBP3 SDS were not significantly correlated with changes in lipid biomarkers or insulin in either group.

IGF-I SDS at Month 1 for GHD

The reported model for predicting IGF-I SDS at 1 month included the following predictive factors:

IGF-I SDS at 1 month=−constant+$a$(IGF-I SDS at baseline)+$b$(Weight SDS at baseline)+$c$(Adherence(%))+$d$(Age at baseline(years))+$e$(GH dose (µg/kg/day))

| Predictive factor | Cumulative adjusted $R^2$ | Coefficient |
| --- | --- | --- |
| Intercept | | −4.7265 |
| IGF-I SDS at baseline | 58.90% | 0.7065 |
| +Weight SDS at baseline | 62.54% | 0.2446 |
| +Adherence (%) | 63.97% | 0.0423 |
| +Age at baseline (years) | 64.95% | 0.057 |
| +GH dose (µg/kg/day) | 66.07% | 0.0402 |

These factors accounted for 66% of the variability (adjusted $R^2$) in IGF-I SDS at 1 month; excluding three outliers gave an adjusted $R^2$ of 76%).

The reported model was then applied in subgroup analyses of genomic markers that have been demonstrated to be associated with IGF-I SDS change to evaluate the variability explained in these sub-populations. The results are as follows:

| Population | N | Adjusted $R^2$ |
| --- | --- | --- |
| All subjects from whom biological, clinical and therapeutic factors were used to derive the short term predictive model | 162 | 66% |
| CDK4 rs2270777 AA genotype | 35 | 81% |
| LEPR rs970467 A allelic | 32 | 71% |

CDK4, cyclin-dependent kinase 4;
LEPR, leptin receptor.

IGF-I SDS at Month 1 for TS

The reported model for predicting IGF-I SDS at 1 month included the following predictive factors:

IGF-I SDS at 1 month=constant+$a$(IGF-I SDS at baseline)+$b$(Weight SDS at baseline)+$c$(GH Dose(µg/kg/day))−$d$(Thyroid replacement therapy)−$e$(Triglycerides at baseline(mmol/L))−$f$(Weight SDS at birth).

| Predictive factor | Cumulative adjusted $R^2$ | Coefficient |
| --- | --- | --- |
| Intercept | | 0.0995 |
| IGF-I SDS at baseline | 33.28% | 0.4371 |
| +Weight SDS at baseline | 42.87% | 0.3661 |
| +GH dose (µg/kg/day) | 44.17% | 0.3080 |
| +Thyroid replacement therapy | 45.85% | −0.6797 |
| +Triglycerides at baseline (mmol/L) | 46.40% | −0.3007 |
| +Weight SDS at birth | 46.64% | −0.0695 |

These factors accounted for 47% of the variability (adjusted $R^2$) in IGF-I SDS at 1 month; excluding one outlier produced an adjusted $R^2$ of 53%

The reported model was then applied in subgroup analyses of genomic markers that have been demonstrated to be associated with IGF-I SDS change to evaluate the variability explained in these sub-populations. The results are as follows:

| Population | N | Adjusted $R^2$ |
|---|---|---|
| All subjects from whom biological, clinical and therapeutic factors were used to derive the short term predictive model | 124 | 47% |
| SH2B2 rs2906713 C allelic | 34 | 56% |
| PIK3CB rs10513055 AA genotype | 91 | 57% |
| CDK4 rs2069502 A allelic | 70 | 57% |
| CDK4 rs2270777 G allelic | 100 | 56% |
| BCL2 rs4456611 GG genotype or SH2B2 rs2906713 C allelic | 49 | 59% |
| BCL2 rs4456611 A allelic and PIK3CB rs10513055 AA genotype | 76 | 56% |
| BCL2 rs4456611 A allelic and CDK4 rs2069502 A allelic | 55 | 57% |
| Karyotype 45X presence | 57 | 61% |

CDK4, cyclin-dependent kinase 4;
PIK3CB, phosphatidylinositol 3' kinase 110-kD catalytic subunit;
SH2B2, SH2B adaptor protein 2,
BCL2, B-cell lymphoma 2 protein.

IGFBP3 SDS at Month 1 for TS

The reported model for predicting IGFBP3 SDS at 1 month included the following predictive factors:

IGFBP3 SDS at 1 month=constant+$a$(IGFBP3 SDS at baseline)−$b$(Age at baseline(years))+$c$(Weight SDS at baseline)−$d$(Triglycerides at baseline (mmol/L))+$e$(TSH at baseline(mIU/L))+$f$(GH dose(μg/kg/day))

| Predictive factor | Cumulative adjusted $R^2$ | Coefficient |
|---|---|---|
| Intercept | | 1.1760 |
| IGFBP3 SDS at baseline | 46.73% | 0.4658 |
| +Age at baseline (years) | 51.08% | 0.0497 |
| +Weight SDS at baseline | 52.45% | 0.0897 |
| +TSH at baseline (mIU/L) | 52.91% | 0.0215 |
| +Triglycerides at baseline (mmol/L) | 53.38% | −0.1820 |
| +GH dose (μg/kg/day) | 53.01% | 0.0032 |

These factors accounted for 53% of the variability (adjusted $R^2$) in IGFBP3 SDS at 1 month; excluding two outliers increased the $R^2$ to 56%)

The reported model was then applied in subgroup analyses of genomic markers that have been demonstrated to be associated with IGFBP3 SDS change to evaluate the variability explained in these sub-populations. The results are as follows:

| Population | N | Adjusted $R^2$ |
|---|---|---|
| All subjects from whom biological, clinical and therapeutic factors were used to derive the short term predictive model | 118 | 53% |
| SH2B2 rs2906713 C allelic | 33 | 66% |
| PIK3CB rs10513055 AA genotype | 89 | 60% |
| BCL2 rs4456611 GG genotype or SH2B2 rs2906713 C allelic | 47 | 64% |
| BCL2 rs4456611 A allelic and PIK3CB rs10513055 AA genotype | 74 | 60% |
| BCL2 rs4456611 A allelic and CDK4 rs2069502 A allelic | 55 | 64% |
| Karyotype 45X absence | 66 | 58% |
| Karyotype i(Xq) absence | 86 | 59% |

CDK4, cyclin-dependent kinase 4;
PIK3CB, phosphatidylinositol 3' kinase 110-kD catalytic subunit;
SH2B2, SH2B adaptor protein 2,
BCL2, B-cell lymphoma 2 protein;

The invention claimed is:

1. A method of treating an individual having Growth Hormone Deficiency (GHD), the method comprising the steps of:
   a) identifying insulin-like growth factor standard deviation score (IGF-I SDS) at treatment baseline ("IGF-I_SDS_B");
   b) setting the treatment adherence in percent of expected doses/planned doses during the first month of treatment ("adherence");
   c) measuring the weight standard deviation score (SDS) at treatment baseline ("bl_wt SDS");
   d) setting the average growth hormone dose prescribed in μg/kg bodyweight/day ("dose");
   e) providing the age in years ("age");
   f) calculating the predicted IGF-I SDS after one month of treatment with growth hormone as IGF-I_SDS_1M=−4.7265+(0.7065×IGF-I_SDS_B)+(0.0423×"adherence")+(0.2446×bl_wt SDS)+(0.0402×"dose")+(0.057×"age");
   g) identifying the individual as a low responder if IGF-I SDS level change at one month compared to the IGF-I_SDS_B is less than 0.81, identifying the individual as a high responder if IGF-I SDS level change at one month compared to the IGF-I_SDS_B is more than 1.91 and identifying the individual as an intermediate responder if IGF-I SDS level change at one month compared to the IGF-I_SDS_B is 0.81 to 1.91; and
   h) administering growth hormone to the individual identified as a low responder or as a high responder.

2. The method according to claim 1, wherein the individual has genotype AA in CDK4_rs2270777 or allele A in LEPR_rs970467.

3. The method according to claim 1, wherein the growth hormone is human growth hormone.

4. The method according to claim 1, said method comprising administering an increased dose of GH as compared to the standard dose or administering long acting analogues of GH to an individual identified as a low responder.

5. The method according to claim 1, said method comprising a daily dosage of GH to an individual identified as a high responder, said daily dosage ranging from about 0.02 mg/kg of body weight up to about 0.07 mg/kg of body weight.

6. The method according to claim 4, said method comprising administering to a low responder an increased dose of GH compared to a standard dose.

7. The method according to claim 4, said method comprising administering to a low responder a long acting analogue of GH.

* * * * *